United States Patent
Rynerson

(10) Patent No.: US 11,819,456 B2
(45) Date of Patent: Nov. 21, 2023

(54) ELECTROLYTIC DEVICE FOR TREATING AN EYE DISORDER

(71) Applicant: James M. Rynerson, Franklin, TN (US)

(72) Inventor: James M. Rynerson, Franklin, TN (US)

(73) Assignee: BLEPHEX, LLC, Brentwood, TN (US)

( * ) Notice: Subject to any disclaimer, the term of this patent is extended or adjusted under 35 U.S.C. 154(b) by 340 days.

(21) Appl. No.: 15/953,616

(22) Filed: Apr. 16, 2018

(65) Prior Publication Data

US 2018/0325729 A1 Nov. 15, 2018

Related U.S. Application Data

(63) Continuation-in-part of application No. PCT/US2016/057112, filed on Oct. 14, 2016.
(Continued)

(51) Int. Cl.
*A61F 9/007* (2006.01)
*A61B 8/14* (2006.01)
(Continued)

(52) U.S. Cl.
CPC .. *A61F 9/00709* (2013.01); *A61B 17/320068* (2013.01); *A61B 18/1206* (2013.01);
(Continued)

(58) Field of Classification Search
CPC ............. A61F 9/00709; A61F 9/00718; A61B 17/320068; A61B 18/1206; A61B 18/14;
(Continued)

(56) References Cited

U.S. PATENT DOCUMENTS 4,326,529 A * 4/1982 Doss ...................... A61B 18/08
606/41
4,406,658 A * 9/1983 Lattin ..................... A61N 1/325
604/20
(Continued)

FOREIGN PATENT DOCUMENTS

CN 1826153 A 8/2006
WO 2011050327 A1 4/2011
(Continued)

OTHER PUBLICATIONS

European Patent Office, International Searching Authority, International Search Report and Written Opinion issued in corresponding PCT Application No. PCT/US2016/057112, dated Jan. 31, 2017 (15 pages).
(Continued)

*Primary Examiner* — Tigist S Demie
(74) *Attorney, Agent, or Firm* — Wilson Sonsini Goodrich & Rosati

(57) ABSTRACT

Devices and methods are described for electrolytically, ultrasonically, or both electrolytically and ultrasonically disrupting debris on an eyelid margin. A device includes an eyelid contacting portion having at least a first electrode, a second electrode, and a power supply electrically coupled to at least one of the first and second electrodes. The eyelid contacting portion may optionally have a shelf separating an upper portion from a lower portion with electrodes on the upper and lower portions. The eyelid contacting portion may optionally include at least one channel with electrodes. The device may optionally include an ultrasonic driver. Another device includes an ultrasonic driver but no electrodes. A method contacts debris on an eyelid margin with a first electrode and contacting a surface of an eyelid with a second electrode and supplying electrical energy to one of the first
(Continued)

or second electrodes to disrupt the debris. Another method applies ultrasonic energy to the eyelid margin to disrupt debris on the eyelid margin.

20 Claims, 13 Drawing Sheets

Related U.S. Application Data

(60) Provisional application No. 62/242,721, filed on Oct. 16, 2015.

(51) Int. Cl.
*A61B 1/32* (2006.01)
*A61B 8/12* (2006.01)
*A61B 17/32* (2006.01)
*A61B 18/12* (2006.01)
*A61B 18/14* (2006.01)

(52) U.S. Cl.
CPC .......... *A61B 18/14* (2013.01); *A61F 9/00718* (2013.01); *A61B 2018/142* (2013.01); *A61B 2018/1472* (2013.01); *A61B 2218/002* (2013.01)

(58) Field of Classification Search
CPC ...... A61B 2018/142; A61B 2018/1472; A61B 2218/002
USPC .......................................................... 606/41
See application file for complete search history.

(56) References Cited

U.S. PATENT DOCUMENTS

| | | | | |
|---|---|---|---|---|
| 4,955,378 A * | 9/1990 | Grasso | ................... | C12N 15/02 604/20 |
| 5,643,197 A * | 7/1997 | Brucker | ............ | A61M 25/0068 604/164.08 |
| 5,840,030 A * | 11/1998 | Ferek-Petric | ...... | A61B 18/1492 607/122 |
| 5,843,147 A * | 12/1998 | Testerman | .......... | A61F 9/00718 607/116 |
| 2002/0128639 A1* | 9/2002 | Pless | ...................... | A61B 18/02 606/41 |
| 2005/0004625 A1 | 1/2005 | Chow | | |
| 2006/0241580 A1* | 10/2006 | Mittelstein | .......... | A61F 9/00781 606/41 |
| 2009/0187184 A1* | 7/2009 | Muller | ............... | A61B 18/1815 606/41 |
| 2013/0006241 A1* | 1/2013 | Takashino | ......... | A61M 5/16804 606/45 |
| 2013/0030385 A1* | 1/2013 | Schultz | ............... | A61M 3/0258 604/247 |
| 2013/0053733 A1* | 2/2013 | Korb | ................... | A61F 9/00718 601/2 |
| 2013/0281967 A1* | 10/2013 | Papay | ................ | A61B 18/1477 604/501 |
| 2014/0031845 A1* | 1/2014 | Rynerson | ................ | A61F 13/38 606/162 |
| 2016/0346029 A1* | 12/2016 | Colquhoun | ............ | A61B 18/00 |

FOREIGN PATENT DOCUMENTS

| | | |
|---|---|---|
| WO | 2014018651 A1 | 1/2014 |
| WO | 2015119715 A2 | 8/2015 |
| WO | WO-2017066620 A1 | 4/2017 |

OTHER PUBLICATIONS

International Preliminary Report on Patentability issued in corresponding PCT Application No. PCT/US2016/057112, dated Apr. 17, 2018.

\* cited by examiner

ELECTROLYTIC DEVICE FOR TREATING AN EYE DISORDER

CROSS REFERENCE TO RELATED APPLICATIONS

This application is a continuation-in-part of Intl. App. No. PCT/US2016/057112 filed on Oct. 14, 2016, published as Intl. Pub. No. WO 2017/066620, and entitled "ELECTROLYTIC DEVICE FOR TREATING AN EYE DISORDER", and claims the benefit of U.S. App. No. 62/242,721 filed on Oct. 16, 2015 and entitled "ELECTROLYTIC DEVICE FOR TREATING AN EYE DISORDER", and the disclosures of which are each incorporated by reference herein in their entireties.

TECHNICAL FIELD

The present invention relates generally to a method and instrument for treating an ocular disorder, and more particularly, to an instrument applying electrical energy, ultrasonic energy, or both electrical and ultrasonic energy for treating eyelid margin disease and methods of using said instrument.

BACKGROUND

Ocular disorders such as those relating to eyelid margin disease are particularly common pathological conditions of the ocular adenexa. By way of example, these disorders include blepharitis, meibomitis, and dry eye syndrome. Eyelid margin disease usually includes a buildup of debris on the eyelid margin of the eye of an individual. The debris may include a biofilm such as secreted by bacteria, as well as scurf, mucus, oils, and other secreted fluids. Despite advances in ophthalmology and medical treatments in general, the recommended treatments for these exemplary common ocular disorders has remained essentially unchanged for decades.

Historically, treating eyelid margin disease focused on a hygienic home treatment procedure in which the patient was to scrub the eyelid margin to remove the debris that is resulting in inflammation. Removal of this debris is critical to both healing the eye and preventing a resurgence of the disorder. Without proper, regular removal of accumulated debris, such ocular disorders regularly worsen despite periodic treatments.

Hygienic home treatment of such ocular disorders is generally a two-step process. First, the patient softens the debris by applying a warm compress, diluted baby shampoo, or a specialized liquid solution to the eyelid margin. This first step is intended to prepare the debris for removal while preventing further irritation to the eye. Second, the patient attempts to remove the debris by physically scrubbing the eyelid margin, the base of the eyelashes, and the pores of the meibomian glands. This scrubbing is routinely attempted with either a generic cotton swab, a fingertip, or a scrub pad placed over the fingertip and applied against the eye. By cleaning debris free from the base of the eyelashes and unclogging the pores of the meibomian glands, the patient may improve the overall health of the eyelid margin; thereby reducing irritation, burning, and other symptoms related to the disorder.

Unfortunately for many patients, such hygienic home treatment is met with limited success due to the practical difficulties of cleaning one's own eye with an imprecise instrument such as a fingertip or cotton swab. For instance, many patients do not have the necessary dexterity to manipulate their fingertip or a cotton swab along the eyelid margin. Moreover, a shake, tremor, or poor near vision further complicate such self-treatment. Even for those capable of incorporating hygienic home treatment into their daily routine, many, if not most people, are wary of placing objects near their eyes to actively scrub along the eyelid margin. Given this anxiety, discomfort, and the inability to specifically target debris, patients routinely fail to totally cleanse the margin of the eyelid, the base of the eyelashes, and the meibomian glands. While the attempted treatment may temporarily abate the patient's symptoms, subtle continuation of the disease often persists; thus permitting a low-grade inflammation to develop and, ultimately lead to chronic dry eye syndrome. In many cases, the debris, including biofilm and other material, is tightly attached to the lid margin by bacteria-produced glue-like proteins, such as adhesin molecules, making it virtually impossible for any type of home remedy to remove it. Further, this treatment is typically required to be performed for the rest of the patient's life; thereby, creating a substantial hurdle to regular and effective compliance during hygienic home treatment.

More recently, devices have been developed for use by medical professionals to scrub debris from the eyelid margins of affected patients. These devices typically employ a motorized scrubbing head that includes a rotary or vibrating movement. The scrubbing head is brought into contact with the eyelid margin to remove debris thereon. While these devices tend to be highly effective at removing debris from the eyelid margin and providing relief to the patient, these treatments may also results in some discomfort as the moving scrubbing head may irritate the eyelid margins of some patients. Moreover, the scrubbing head does not address debris, including a biofilm or excess bacteria, within the meibomian gland, lash follicle or lacrimal glands.

There is a need for a method and apparatus for use in treating ocular disorders, such eyelid margin diseases, that addresses present challenges and characteristics such as those discussed above.

SUMMARY

The present invention provides an improved method and device for removing debris from the eyelid margin of a patient. An aspect of the invention is directed to a device for electrolytically disrupting debris on an eyelid margin. The device includes an eyelid contacting portion having a surface that includes at least a first electrode and a second electrode. The device further includes a power supply electrically coupled to at least one of the first and second electrodes. The surface of the eyelid contacting portion may optionally have a shelf separating an upper portion from a lower portion with electrodes on the upper and lower portions and on upper and lower surfaces of the shelf. The eyelid contacting portion may optionally include at least one channel with electrodes.

Another aspect of the invention is direct to a method of electrolytically removing debris from an eyelid margin of a subject. The method includes contacting debris on an eyelid margin with a first electrode and contacting a surface of an eyelid adjacent to but spaced apart from the debris with a second electrode and supplying electrical energy to one of the first or second electrodes in an amount sufficient to disrupt the debris while not harming the underlying eyelid margin or eyelid.

Another aspect of the invention is directed to a device for ultrasonically disrupting debris on an eyelid margin. The device includes an eyelid contacting portion having a surface that is coupled to an ultrasonic driver. The surface of the eyelid contacting portion may optionally have a shelf separating an upper portion from a lower portion. The eyelid contacting portion may optionally include at least one channel. The eyelid contacting portion may optionally include with electrodes for applying electrical energy in addition to ultrasonic energy.

Another aspect of the invention is direct to a method of ultrasonically removing debris from an eyelid margin of a subject. The method includes contacting debris on an eyelid margin with an eyelid contacting portion of an instrument and supplying ultrasonic energy to one of the eyelid contacting portion in an amount sufficient to disrupt the debris while not harming the underlying eyelid margin or eyelid.

These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

DETAILED DESCRIPTION

Figure 1:
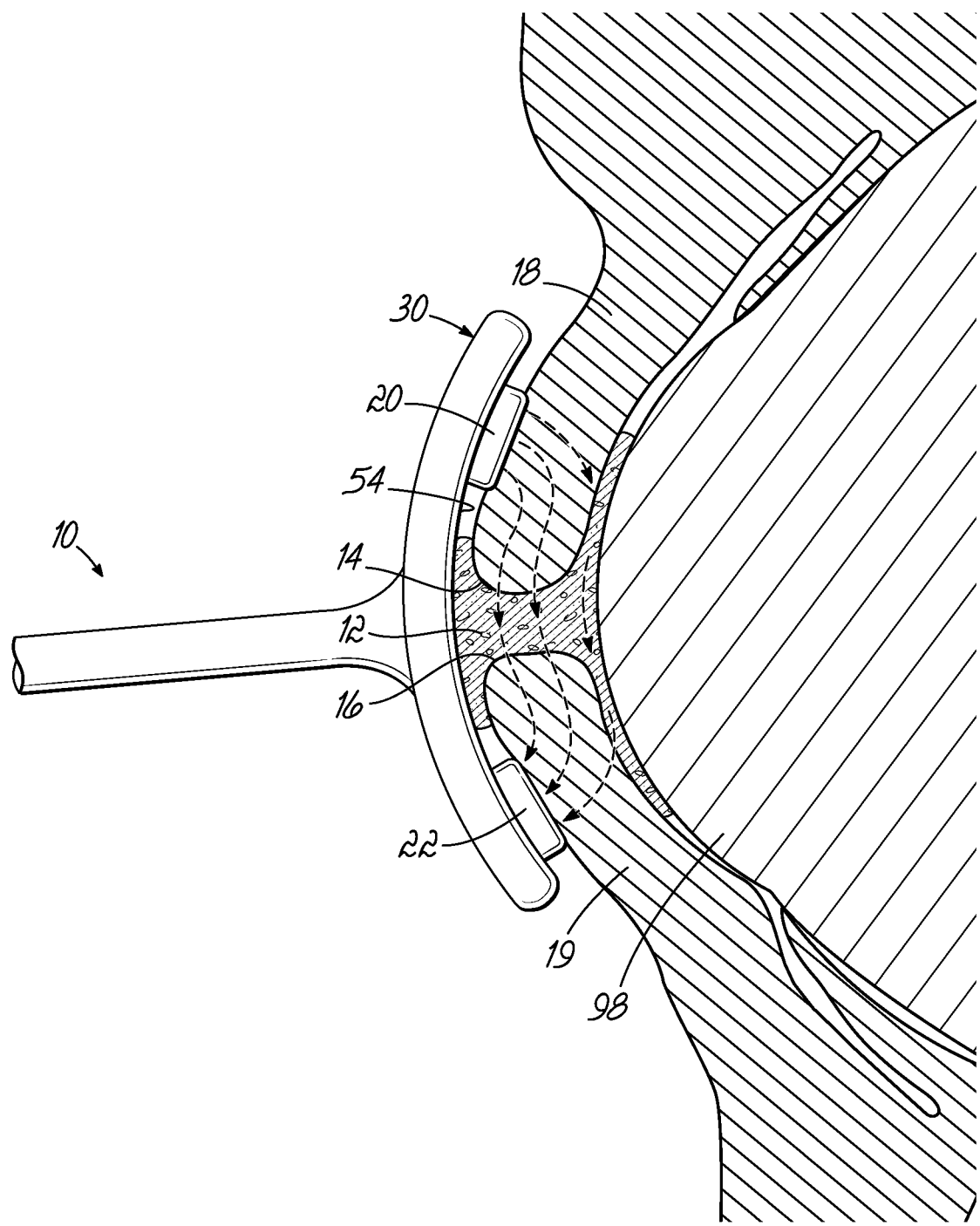
FIG. 1 is a cross-sectional side view of a portion of an embodiment of the device in use in accordance with an aspect of the invention.

The Detailed Description refers to accompanying drawings to illustrate exemplary embodiments consistent with the present disclosure. References in the Detailed Description to "one exemplary embodiment," "an exemplary embodiment," an "example exemplary embodiment," etc., indicate that the exemplary embodiment described may include a particular feature, structure, or characteristic, but every exemplary embodiment may not necessarily include the particular feature, structure, or characteristic. Moreover, such phrases are not necessarily referring to the same exemplary embodiment. Further, when a particular feature, structure, or characteristic is described in connection with an exemplary embodiment, and it is within the knowledge of those skilled in the art(s) to affect such feature, structure, or characteristic in connection with other exemplary embodiments whether or not explicitly described, such other embodiments, so affected, are intended to be suggested and included in this description.

The exemplary embodiments described herein are provided for illustrative purposes, and are not limiting. Other exemplary embodiments are possible, and modifications may be made to the exemplary embodiments within the spirit and scope of the present disclosure. Therefore, the Detailed Description is not meant to limit the present disclosure. Rather, the scope of the present disclosure is defined only in accordance with the following claims and their equivalents.

The Detailed Description of the exemplary embodiments will so fully reveal the general nature of the present disclosure that others can, by applying knowledge of those skilled in the relevant art(s), readily modify and/or adapt for various applications such exemplary embodiments, without undue experimentation, without departing from the spirit and scope of the present disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

With reference to FIGS. 1 to 10, an aspect of the invention is directed to devices 10, 10a for electrolytically disrupting debris 12, that includes, but is not limited to, includes at least one of a biofilm, bacteria, scurf, keratinization, dead cells, and secreted fluids, along the upper eyelid margin 14, the lower eyelid margin 16, or both the upper and lower eyelid margins 14, 16 of an eye 18 of a subject. With reference to FIGS. 1, 5, 8, and 12 embodiments of the invention include electrodes 20, 20a, 20b, 20c, 22, 22a, 22b, 22c, 24, 24a, 26, 26a on an eyelid contacting portion 30 to contact the one or both of the upper eyelid 32 and the lower eyelid 34 of a subject to apply low voltage and low current electrical energy to the eyelids 32, 34. The electrical energy passes, illustrated as arrows with dashed lines, from one or more anode electrodes through the eyelid(s) and debris on the eyelid margin to one or more cathode electrodes. The electrical energy passing through the debris 12 disrupts the debris 12 and allows for disrupted debris to be easily removed, such as with a wash solution (FIGS. 8 and 12) or by wiping with a tissue or towel. In some embodiments, the device includes nozzles (FIGS. 8 to 13) for applying the wash solution to the eyelid margin to remove the disrupted debris.

In an embodiment of the invention, the voltage of the electrical energy applied to disrupt the debris 12 is in the range from about 0.1 V to about 20 V. In another embodiment, the voltage applied to disrupt the debris 12 is in the range from about 0.1 V to about 10 V. In another embodiment, the voltage applied to disrupt the debris 12 is in the range from about 0.1 V to about 5 V. In another embodiment, the voltage applied to disrupt the debris 12 is in the range from about 0.1 V to about 3 V. In another embodiment, the voltage applied to disrupt the debris 12 is in the range from about 0.1 V to about 2 V. In another embodiment, the voltage applied to disrupt the debris 12 is in the range from about 0.1 V to about 1 V. In another embodiment, the voltage applied to disrupt the debris 12 is in the range from about 0.5 V to about 10 V. In another embodiment, the voltage applied to disrupt the debris 12 is in the range from about 1 V to about 10 V. In another embodiment, the voltage applied to disrupt the debris 12 is in the range from about 2 V to about 10 V. In another embodiment, the voltage applied to disrupt the debris 12 is in the range from about 3 V to about 10 V. In another embodiment, the voltage applied to disrupt the debris 12 is in the range from about 5 V to about 10 V. In another embodiment, the voltage applied to disrupt the debris 12 is in the range from about 10 V to about 20 V.

In an embodiment of the invention, the current applied to disrupt the debris 12 is less than about 3 milliamps. In another embodiment of the invention, the current applied to disrupt the debris 12 is in a range from about 0.1 milliamps to about 3 milliamps. In another embodiment of the invention, the current applied to disrupt the debris 12 is in a range from about 0.5 milliamps to about 3 milliamps. In another embodiment of the invention, the current applied to disrupt the debris 12 is in a range from about 1 microamp to about 3 milliamps.

With reference to FIGS. 2, 3, 8, 11, and 14 embodiments of the device 10, 10*a*, 10*b* include a power supply 40 to supply electrical energy to the electrodes 20, 22, 24, 26. Embodiments of the device 10, 10*a*, 10*b* may also include hardware, software, or any combination thereof that may be used to control the electrical energy being supplied to the electrodes. The hardware, such as a controller 42, may include software and be electrically coupled to the power supply 40 and the electrodes 20, 22, 24, 26. Embodiments of the device 10, 10*a*, 10*b* may also include instructions supplied by a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical optical, acoustical or other forms of propagated signals (e.g., carrier waves, infrared signals, digital signals, etc.), and others. Further software routines and instructions may be described herein as performing certain actions. However, it should be appreciated that such descriptions are merely for convenience and that such actions in fact result from computing devices, processors, controllers 42, or other devices executing the software, routines, instructions, etc.

In an embodiment, the device 10, 10*a*, 10*b* may include a user interface 43 that includes an input system and a display system. The input system allows the user to adjust the operation of the device 10, 10*a*, 10*b* and, in some embodiments, interact with the controller 42 to control the device 10, 10*a*. For example, the user interface 43 may allow the user to activate the supply of electrical energy to the electrodes 20, 22, 24, 26, to increase or decrease the electrical energy being supplied to the electrodes 20, 22, 24, 26, increase or decrease the duration of treatment, activate a pump controlling the flow of wash solution from a reservoir 44 to nozzles 36 (FIG. 11), activate a pump controlling the flow of waste fluid from irrigation ports 37 to a waste fluid receptacle such as a waste fluid reservoir 75 or sink (FIG. 8), and combinations thereof. The input system may include at least one of a button 46, a dial, a trigger 48, a switch, a touch screen and other input devices as are known in the electrical arts. The display system conveys information to the user with respect to the status of the device. In an embodiment, the display may include one or more lights 52 such as light emitting diodes, an LCD display 47 (FIG. 13), gauges, or other types of displays as are known in the art. For example, the device 10, 10*b* may include one or more lights 52 to indicate the powered on status of the device 10, 10*b*, indicate the level of energy remaining in the power supply, such as in a battery, or if the electrodes are making sufficient contact with the skin of the subject undergoing treatment.

Figure 3:
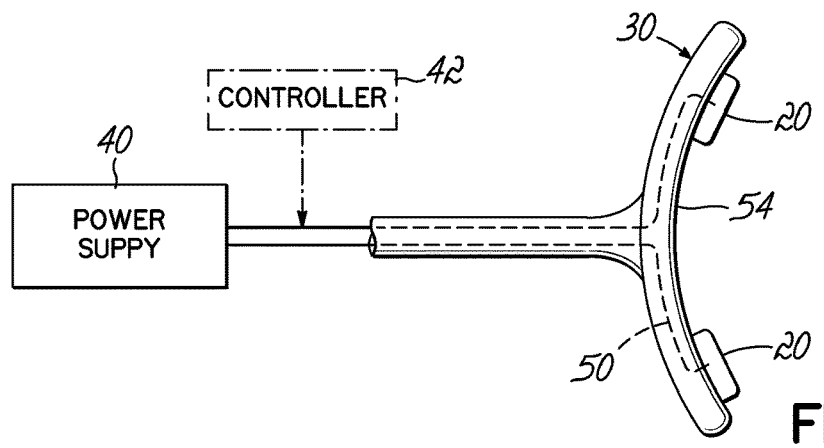
FIG. 3 is an enlarged side view of the eye contacting portion of the instrument of FIG. 2 including a controller.
Figure 4:
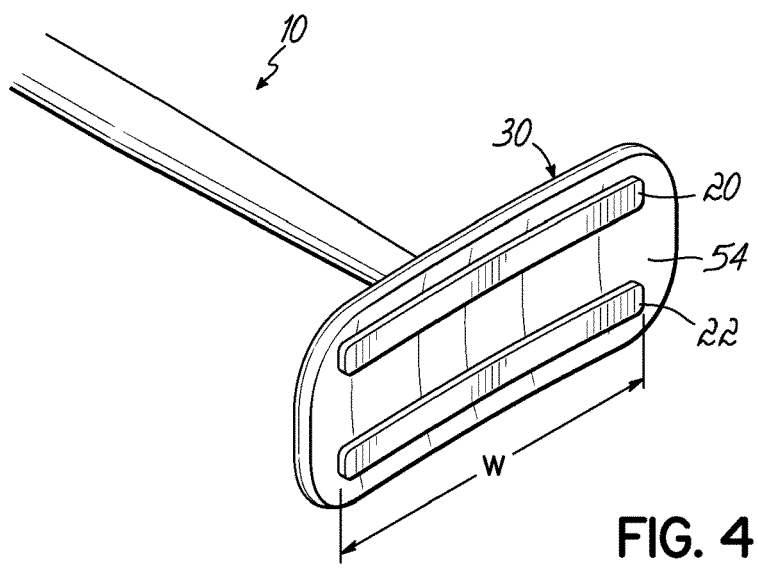
FIG. 4 is an enlarged perspective view of the eye contacting portion of the instrument of FIG. 2.

As illustrated in FIG. 3, the controller 42, power supply 40, user interface (e.g., lights 52, buttons, 46, and triggers 48) may be contained in a housing 55, 55*a* shaped in the form of a handle from which the eyelid contacting portion 30, 30*a*, 30*b*, 30*c* projects. It will be appreciated that the controller, power supply, user interface, and other components may be in one or more housings and the one or more housings need not be in the form of a handle. For example, in the embodiment illustrated in FIG. 13, the housing with one or more components may be a base unit 57 that can be located some distance away from the subject but that is also electrically coupled to the eyelid contacting portion by a flexible member, such as an electric cable. The base unit 57 may optionally be fluidly coupled to the eyelid contacting portion by one or more flexible tubes to allow for the delivery of wash fluid, the removal of waste fluid, and combinations thereof for eyelid contacting portion having such functionality.

With reference to FIGS. 1 to 4, an embodiment of the device 10 for treating an ocular disorder, particularly with respect to eyelid margin diseases, includes an eye contacting portion 30 with a surface 54 that includes a first electrode 20 and a second electrode 22. The surface 54 of the eye contacting portion 30 may be curved to generally correspond to the external curvature of the eye and in particular, the curvature of the upper and lower eyelids 18, 19 so that the first electrode 20 may make contact across the outer surface of the upper eyelid 18 and the second electrode 22 may make contact with the outer surface of lower eyelid 19 when the eyelids 18, 19 are in a closed position. Each of the first and second electrodes 20, 22 has a width W that generally corresponds to the width of the each of the upper and lower eyelids 18, 19. In an embodiment, each of the first and second electrodes 22, 22 has a width W that ranges from 2 cm to about 5 cm. One of the first electrode or second electrodes 20, 22 functions as a cathode and the other of the first electrode or second electrodes 20, 22 functions as an anode. The first and second electrodes 20, 22 are electrically coupled to a circuit 50 that includes a power supply 40 (FIG. 3).

With reference to FIG. 1, during use, electrical energy (arrows with broken lines) flows from the first electrode 20 through the upper eyelid 18 and the upper eyelid margin 14 to the debris 12. The electrical energy then passes through and disrupts the debris 12 before passing through the lower eyelid margin 16 and lower eyelid 19 to the second electrode 22. One of ordinary skill in the art will appreciate that the electrical energy could flow in the opposite direction from the second electrode 22 to the first electrode 20 if the second electrode 22 is the anode and the first electrode is the cathode.

In an embodiment, an electrolyte solution may be added to the eye, such as between the upper and lower eyelid margins 14, 16, to improve the disruption of debris 12 by the electrical energy.

Figure 5:
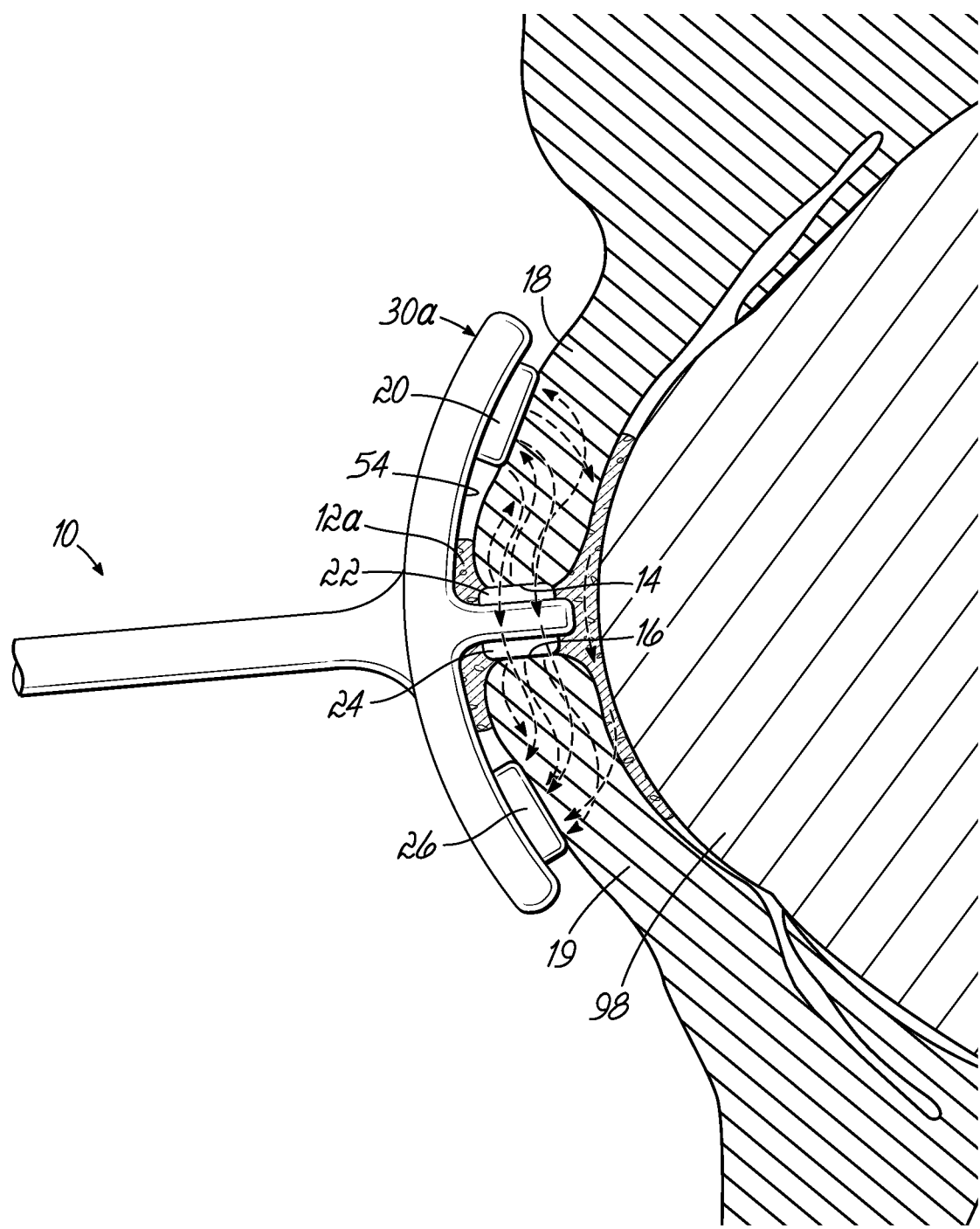
FIG. 5 is a cross-sectional side view of an alternative embodiment of the eye contacting portion in use.
Figure 6:
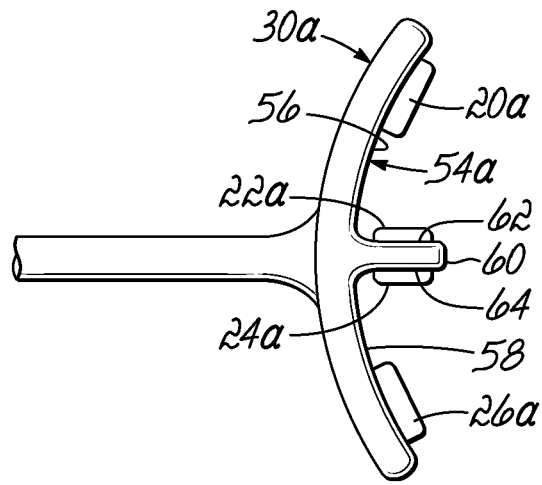
FIG. 6 is a side view of the eye contacting portion of the instrument of FIG. 5.
Figure 7:
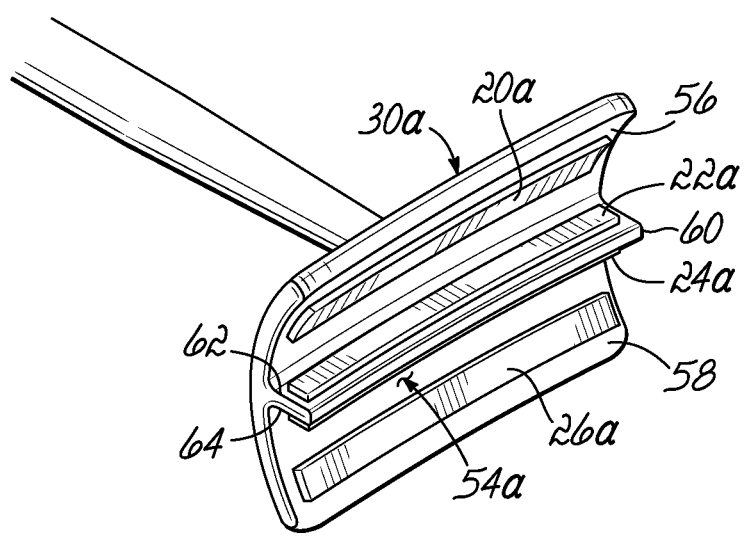
FIG. 7 is a perspective drawing of an alternative embodiment of the eye contacting portion of FIG. 5.

FIGS. 5, 6, and 7 illustrate an alternative embodiment of the eye contacting portion 30a of the device 10. In the alternative embodiment, the surface 54a of the eye contacting portion 30a is separated into an upper portion 56 and a lower portion 58 by a shelf 60. The shelf 60 has an upper shelf surface 62 and a lower shelf surface 64. The upper portion 56 includes a first electrode 20a and the upper shelf surface 62 adjacent the upper portion 56 includes a second electrode 22a. One of the first or second electrodes 20a, 22a will be an anode and the other of the first or second electrodes 20a, 22a will be a cathode. Similarly, the lower portion 58 includes a third electrode 24 and the lower shelf surface 64 includes a fourth electrode 26. One of the third or fourth electrodes 24, 26 will be an anode and the other of the third or fourth electrodes 24, 26 will be a cathode. The first, second, third, and fourth electrodes 20a, 22a, 24, 26 are electrically coupled to a circuit that includes a power supply.

During use, the second electrode 22a on the upper shelf surface 62 contacts the upper eyelid margin 14 of the upper eyelid 18 and may be curved to generally correspond with the curvature of the upper eyelid margin 14. The second electrode 22a will also contact debris 12 along the upper eyelid margin 14 of the upper eyelid 18. Similarly, the fourth electrode 26 on the lower shelf surface 64 contacts the lower eyelid margin 16 of the lower eyelid 19 and may be curved to generally correspond with the curvature of the lower eyelid margin 16. As with the previous embodiment, the first and third electrodes 20a 24 each have a width that corresponds generally with the widths of the respective upper and lower eyelids 18, 19. Similarly, the second and fourth electrodes 22a, 26 on the upper and lower shelf surfaces 62, 64 each have a length and a width that generally corresponds with the length and width of the respective upper and lower eyelid margins 14, 16 for the upper and lower eyelids 18. In an embodiment, the widths of each of the first, second, third, and fourth electrodes 20a, 22a, 24, 26 may range between about 2 cm and about 5 cm. In an embodiment, the lengths of the second and fourth electrodes may range between about 0.5 mm and 3 mm, or between about 1 mm and about 2 mm.

In the embodiment illustrated in FIG. 5, the second and fourth electrodes 22, 26 on the upper and lower shelf surfaces 62, 64, respectively, are anodes and the first and third electrodes 20a, 24 on the upper and lower portions 56, 58 of surface 54a are cathodes, when the device utilizes a direct current power source. Electrical current flows from the anodes through debris 12 on or near the upper and lower eyelid margins 14, 16 to disrupt the debris 12. The electrical current then travels through the upper and lower eyelids 18, 19 to the cathode to complete the circuit. The power supply, which may be a battery or other source of electricity, provides electrical energy to the anodes. It will be appreciated that the polarity of the electrodes may be reversed. It will also be appreciated that an alternating current power source, which will obviate the anode cathode designation of the electrodes.

Figure 8:
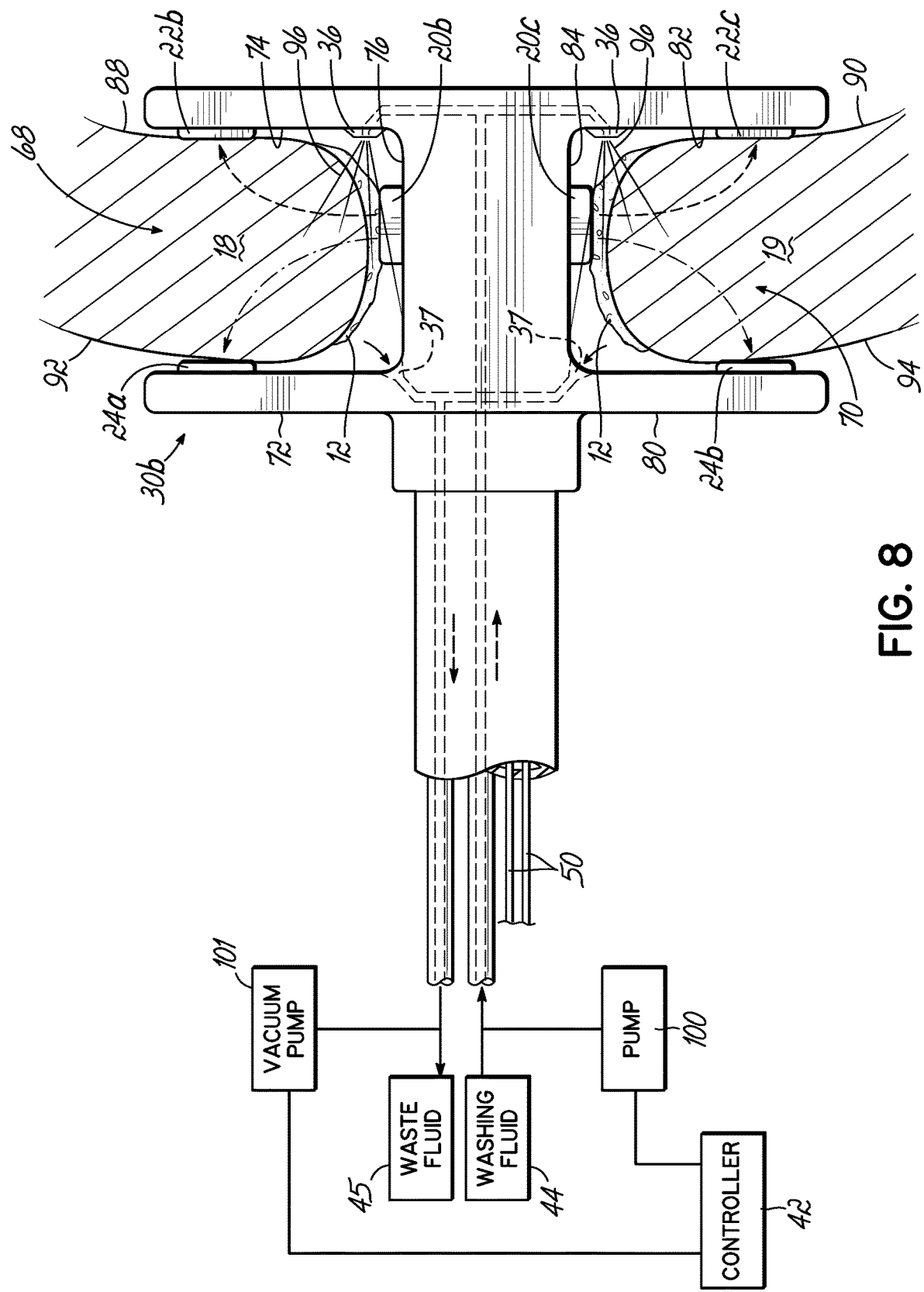
FIG. 8 is a cross-sectional side view of an alternative embodiment of the eye contacting portion in use and including the controller of FIG. 3 in communication with a washing fluid pump and a vacuum pump.
Figure 9:
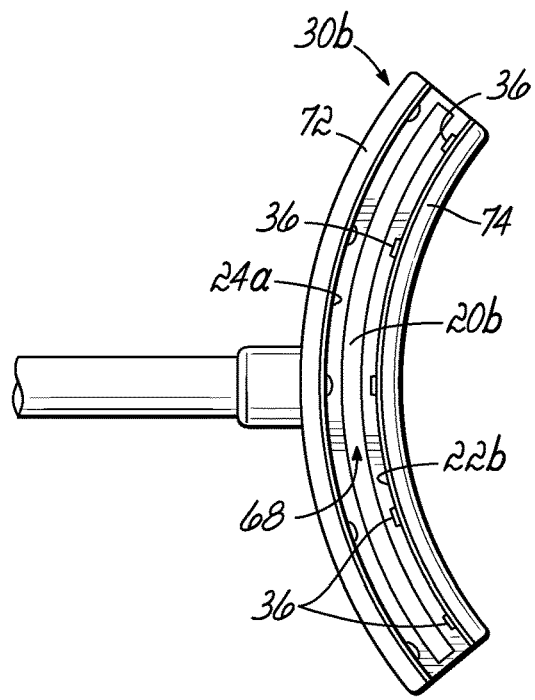
FIG. 9 is top view of the eye contacting portion of the instrument of FIG. 8.
Figure 10:
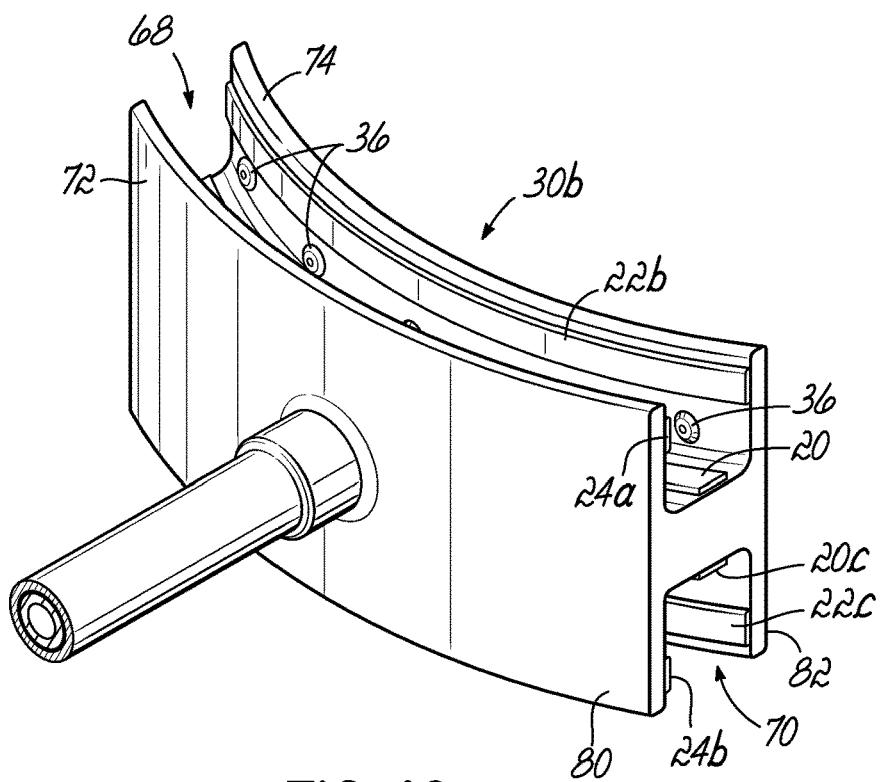
FIG. 10 is a perspective drawing of an alternative embodiment of the eye contacting portion of FIG. 8.

FIGS. 8, 9, and 10 illustrate an alternative embodiment of the eye contacting portion 30b of the device 10. In the alternative embodiment, the eye contacting portion 30b is separated into an upper channel 68 and a lower channel 70.

The upper channel 68 is defined by an upper outer sidewall 72 and an opposite upper inner sidewall 74. The upper outer sidewall 72 is joined to the upper inner sidewall 74 by an upper base wall 76. The upper base wall 76 includes a first electrode 20b. One of the upper outer and upper inner sidewalls 72, 74 includes a second electrode 22b. In an embodiment, both of the upper outer and upper inner sidewalls 72, 74 include an electrode, with one of the upper sidewalls including the second electrode 22b and the other upper sidewall including a third electrode 24a. One of the first and second electrodes 20b, 22b will be an anode and the other of the first or second electrodes 20b, 22b will be a cathode. In embodiments with a third electrode 24a, the third electrode 24a will have the same polarity as the second electrode 22b. In other words, if the second electrode 22b is a cathode, the third electrode 24a will also be a cathode.

The lower channel 70 is defined by a lower outer sidewall 80 and an opposite lower inner sidewall 82. The lower outer sidewall 80 is joined to the lower inner sidewall 82 by a lower base wall 84. The lower base wall 84 includes a first electrode 20c. One of the lower outer and lower inner sidewalls 80, 82 includes a second electrode 22c. In an embodiment, both of the lower outer and lower inner sidewalls 80, 82 include an electrode, with one of the lower sidewalls including the second electrode 22c and the other lower sidewall including a third electrode 24b. One of the first and second electrodes 20c, 22c will be an anode and the other of the first or second electrodes 20c, 22c will be a cathode. In embodiments with a third electrode 24b, the third electrode 24b will have the same polarity as the second electrode 22c. In other words, if the second electrode 22c is a cathode, the third electrode 24b will also be a cathode.

During use, the upper eyelid 18 of a subject is inserted into the upper channel 68 and the lower eyelid 19 of the subject is inserted into the lower channel 70. The inner surfaces 88, 90 of the respective upper and lower eyelids 18, 19 will contact electrodes located on the respective upper and lower inner sidewalls 74, 82. The outer surfaces 92, 94 of the respective upper and lower eyelids 18, 19 of the subject will contact electrodes that may be located on the respective upper and lower outer sidewalls 92, 94. The upper and lower eyelid margins 14, 16 of the respective upper and lower eyelids 18, 19, as well as debris 12 on the eyelid margins 14, 16 will contact the electrodes on the upper and lower base walls 76, 84. Electrical current will flow from the anodes through the debris and eyelid to the cathodes.

Figure 11:
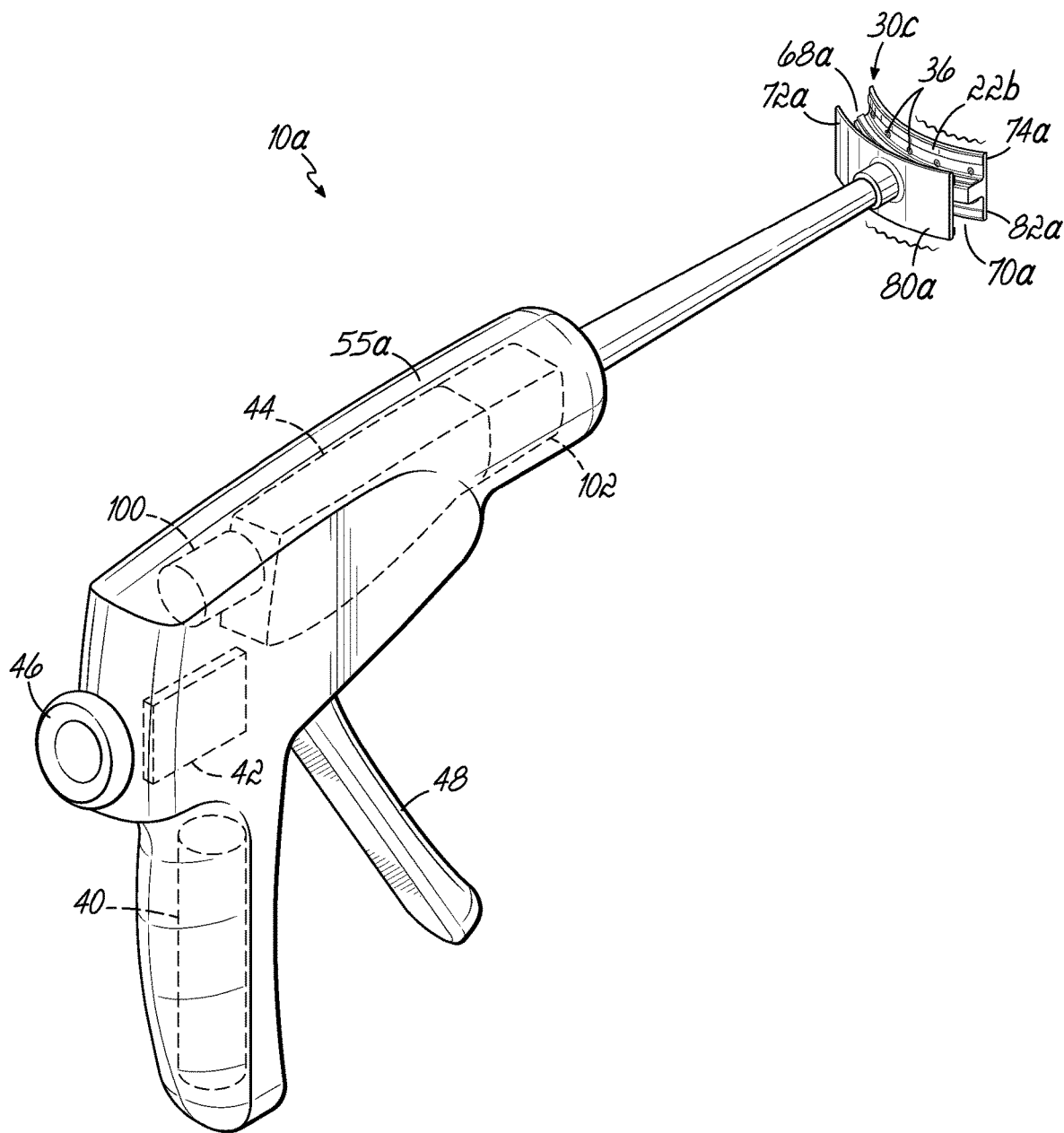
FIG. 11 is a perspective drawing of an alternative embodiment of the device.
Figure 12:
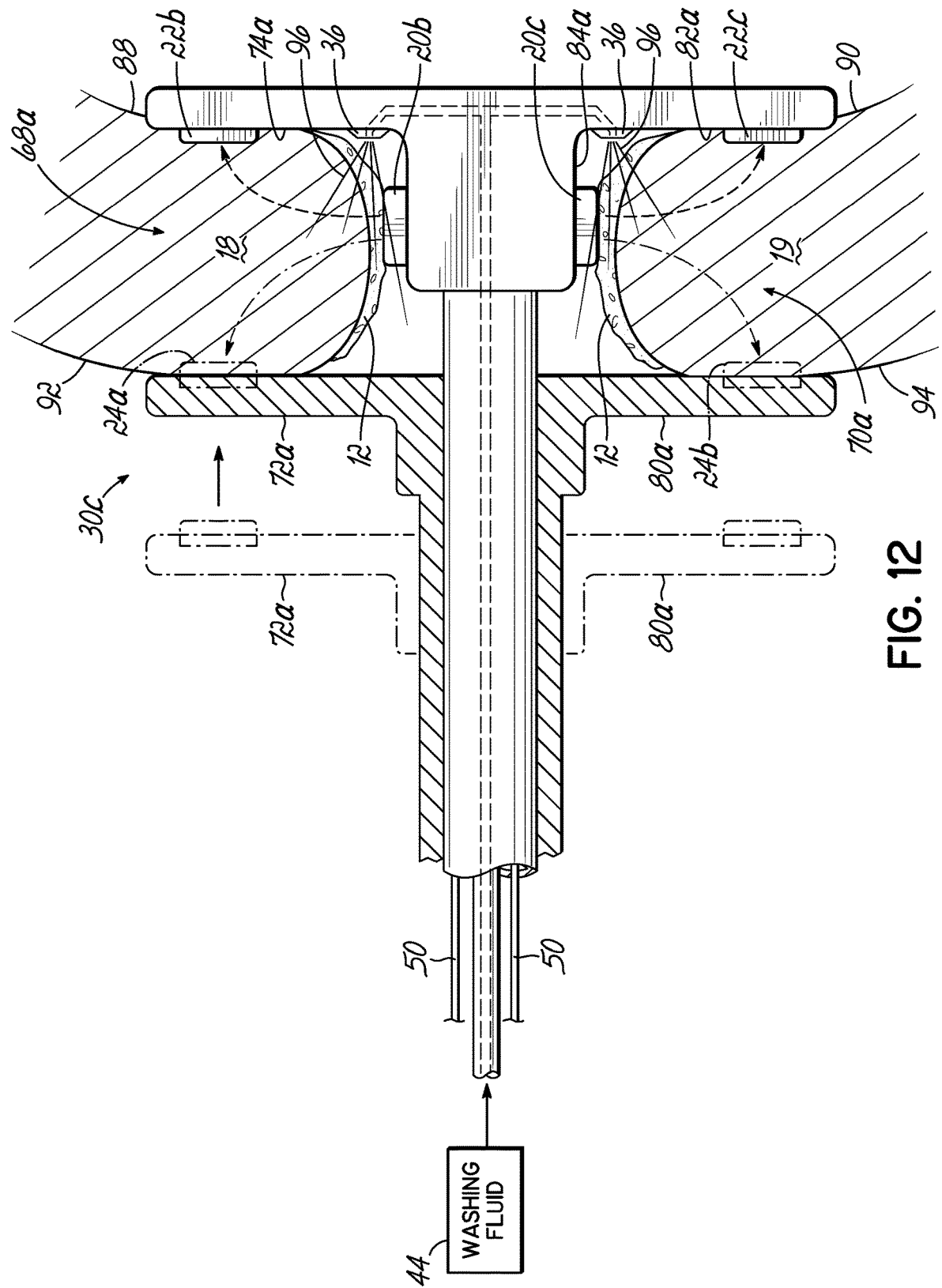
FIG. 12 is a cross-sectional side view of the instrument of FIG. 8 in use.
Figure 13:
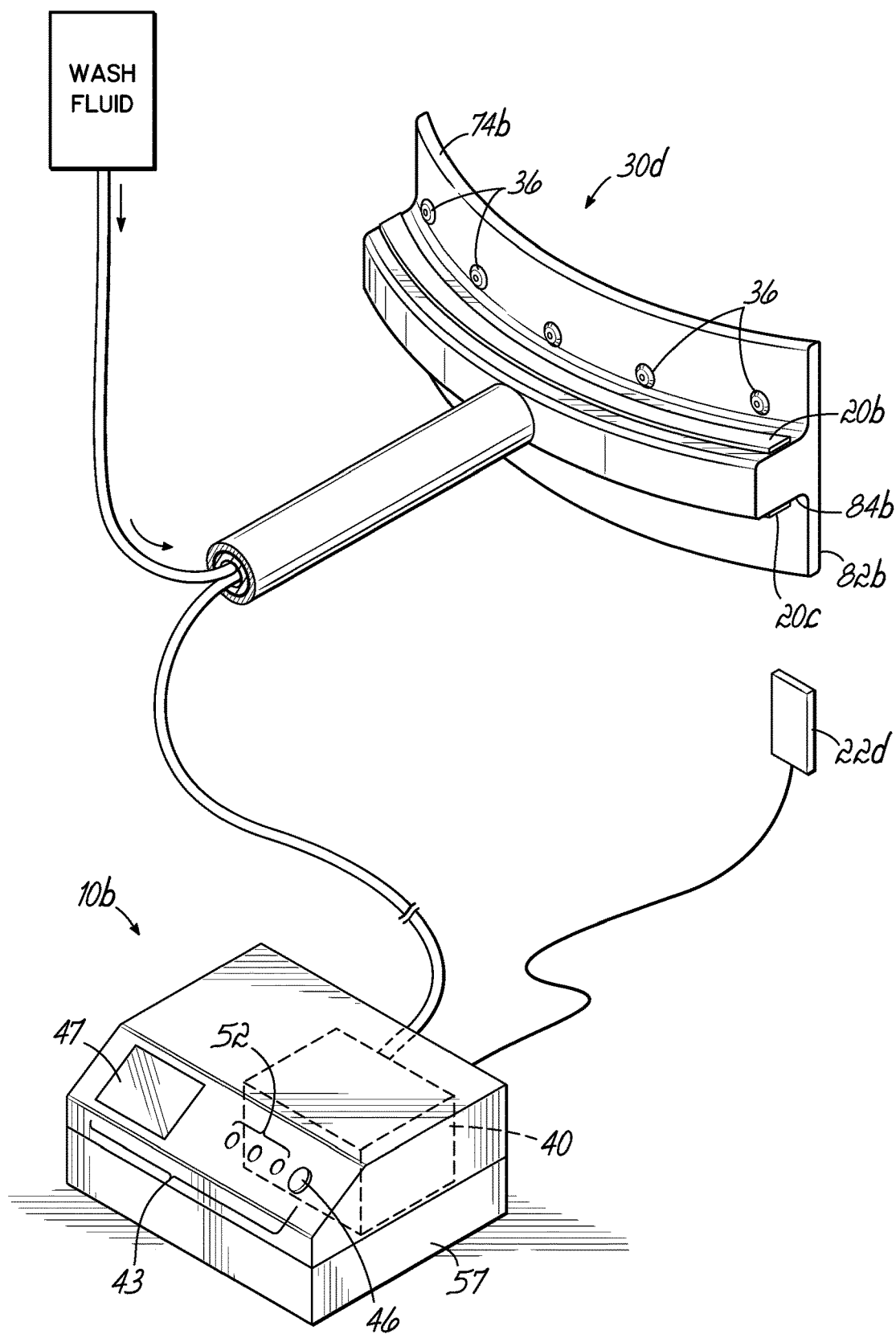
FIG. 13 is a perspective drawing of an alternative embodiment of the device.

Alternative embodiments, such as illustrated in FIGS. 8-13, may include one or more nozzles 36 in the upper and lower channels 68, 70 to spray a wash solution 96, such as a balanced salt solution, across the upper and lower eyelid margins 14, 16 to assist with removing disrupted debris along the upper and lower eyelid margins 14, 16. In an embodiment, the nozzles 36 are positioned in the upper and lower inner sidewalls 74, 74a, 82, 82a to spray wash solution 96 away from the eyeball 98 to wash disrupted debris away. The nozzles 36 will be in fluid communication with a wash solution reservoir 44 (FIGS. 8 and 11). The wash solution 96 may be pushed through the nozzles 36 with a pump 100. The pump 100 may be operated by the controller 42. In the alternative, the wash solution may be gravity fed to the nozzles 36 (FIG. 13).

Alternative embodiments, such as illustrated in FIGS. 8-10, may also include one or more irrigation ports 37 in the upper and lower channels in the upper and lower channels 68, 70 to remove wash solution 96 and debris from the channels and to decreases the overflow of wash fluid and debris into the eye and onto the face of the subject. The irrigation ports 37 may be in fluid communication with a waste fluid receptacle such as a waste fluid reservoir 45 or sink (FIG. 8). The drained wash solution 96 may be drawn into the irrigation ports 37 by a pump, such as vacuum pump 101. The pump, such as vacuum pump 101, may be operated by the controller 42.

FIGS. 11 and 12 illustrate an alternative embodiment of the device that includes upper and lower channels 68a, 70a similar to the upper and lower channels 68, 70 in the embodiment illustrated in FIGS. 8, 9, and 10. As best illustrated in FIG. 12, the upper and lower outer sidewalls 72a, 80a in this alternative embodiment may move relative to the upper and lower base walls 76a, 84a and upper and lower inner sidewalls 74a, 82a. This movement allows the upper and lower channels 68a, 70a to open to ease insertion of the upper and lower eyelids 18, 19 into the respective upper and lower channels 68a, 70a. After the upper and lower eyelids 18, 19 are inserted into the respective upper and lower channels 68a, 70a, the upper and lower outer sidewalls 72a, 80a may be move toward the upper and lower inner sidewalls 74a, 82a, such as the through a trigger 48 coupled to a mechanism for moving the upper and lower outer sidewalls 72a, 80a until the sufficient contact is made with the electrodes in the upper and lower channels 68a, 70a. The electrodes and nozzles 36 may be activated to remove debris 12 as discussed above with respect to the embodiment disclosed in FIGS. 8, 9, and 10.

While the embodiments illustrated in FIGS. 8-12 are shown as having upper and lower channels 68, 68a, 70, 70a, it will be appreciated that embodiments of the device 10 and 10a may be made with a single channel to allow for treatment of one eyelid at a time.

FIG. 13 illustrates an alternative embodiment of the eyelid contacting portion 30d of the device 10b. In this embodiment, upper and lower inner side walls 74b and 82b are separated by shelf having upper and lower base walls 76b and 84b. The eyelid connecting portion 30d is configured to be positioned such that the upper and lower inner side walls 74b and 82b are placed between the inner surface of the eyelid and the outer surface of the eyeball. An electrode 20b, such as an anode, is positioned on the upper base wall 76b and another electrode 20c, such as another anode, is position on the lower base wall 84b. In an embodiment, the electrodes 20b, 20c on the upper and lower base walls 76b, 84b are generally of the same polarity, i.e., either both anodes or both cathodes. During use, the eyelid contacting portion 30d is positioned such that the margin of the eyelid of the upper eyelid, as well as debris thereon, contacts the electrode 20b on the upper base wall 76b and the margin of the eyelid of the lower eyelid, as well as debris thereon, contacts the electrode 20c on the lower base wall.

The electrodes 20b, 20c on the eyelid contacting portion 30d are electrically coupled to a base unit 57 by a flexible member, such as an electric cable. In the exemplary embodiment, the flexible member projects from the shelf such that, during use, the flexible member projects between the upper and lower eyelids of the subject.

This embodiment also utilizes another electrode 22d that is separate from the eyelid contacting portion 30d. Generally speaking, this electrode will have an opposite polarity from the polarity of the electrodes 20b, 20c on the eyelid contacting portion 30d. In an embodiment, the electrodes 20b, 20c on the eyelid contacting portion 30d are anodes and the electrode 22d is a cathode. In another embodiment, the electrodes 20b, 20c on the eyelid contacting portion 30d are cathodes and the electrode 22d is an anode. The electrode 22d may include an electrolyte, such as an electrolytic gel, an adhesive, or an electrolytic adhesive to improve contact with the skin. Electrodes as are known in the art may be utilized for this purpose. The electrode 22d is electrically coupled to the base 57 with an electric cable. During use, the electrode 22d is position adjacent the eye being treated with the eyelid contacting portion 30d. In an embodiment, the electrode 22d is position between 1 inch and 2 inches from margin of the lower eyelid. In an embodiment, the electrode is position below the eye being treated. In another embodiment, the electrode 22d is position lateral to the eye being treated. In another embodiment, the electrode 22d is position above the eye being treated.

In an embodiment, the eyelid contacting portion includes one or more wash fluid nozzles 36. In an embodiment, the wash nozzles are located along the upper and lower inner side walls 74b and 82b on the surface that faces the inner surface of the eyelid such that washing fluid expelled from the nozzles 36 will wash away debris disrupted by the electrodes 20b, 20c. The wash fluid nozzles 36 are fluidly coupled to a reservoir of washing fluid by a flexible tube. In an embodiment, the flexible tube connects to a luer lock that projects from the shelf of the eyelid connecting portion. In an embodiment, the wash fluid reservoir is positioned at a height that is greater than the treatment height of the patient so that washing fluid is gravity fed to the fluid from the nozzles 36. It will be appreciated that a pump could be used to pump the washing fluid from a reservoir to the nozzles.

It will be appreciated that the electrodes may be made from materials as are known in the art for transmitting electrical energy to the surfaces of the skin. For example, the electrodes can be made of a number of materials, such as metals, carbon graphite electrodes, and electrically conducting rubber sheets. Exemplary metals include gold, silver, and other biologically tolerated metals and alloys thereof.

In embodiments of the invention, the eyelid contacting portions 30, 30a, 30b, 30c, 30d may be removable from the housing such that the eyelid contacting portions may be disposed of after a single use or, if reused, sterilized between uses. As such, an embodiment of the invention is directed to removable eyelid contacting portions that are configured to be reversibly coupled to a housing. Such removable eyelid contacting portions may have an electrical coupling, such a male or female electrical contact that mates with a corresponding electrical contact on the housing. The removable eyelid contacting portions may also have a contacting surface having a shape that mates with a correspondingly shaped contacting surface on the housing.

Embodiments of the invention utilize only electrical energy to disrupt debris without utilizing other forms of energy to result in debris disruption. As described above, alternative embodiments may utilize electrical energy to disrupt debris in combination with a wash fluid to assist with debris disruption, to remove debris, or both to disrupt and remove debris.

Figure 2:
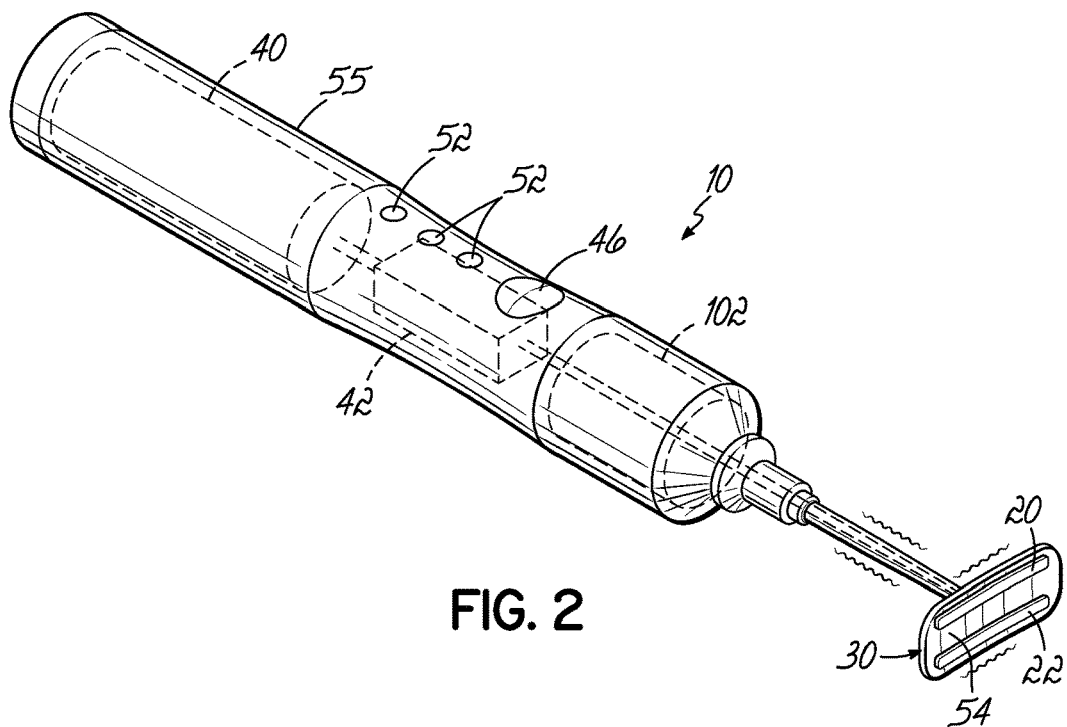
FIG. 2 is a perspective view of an embodiment of the device.

Another embodiment of the invention may include an ultrasonic driver 102 coupled to the eyelid contacting portion to induce ultrasonic movement of an eyelid contacting portion (FIGS. 2 and 11). Embodiments of the invention will utilize the ultrasonic driver 102 in combination with electrical energy applied through electrodes to disrupt debris. Accordingly, these devices will include electrodes, as described above as well as an ultrasonic driver. Other embodiments of the invention will utilize only the ultrasonic driver 102 to induce ultrasonic movement of the eyelid contacting portion to disrupt debris without applying electrical energy to the eye through electrodes to disrupt debris. Accordingly, these embodiments of the device will have an ultrasonic driver but will lack electrodes.

The embodiments utilizing an ultrasonic driver 102 may optionally utilize a wash fluid delivered through nozzles 36 to assist with disrupting, removing, or both disrupting and removing debris. Accordingly, embodiments of the device utilizing a wash fluid will include nozzles, a reservoir, and pump, as previously described. These embodiments may also optionally utilize irrigation ports 37 to remove fluids, such as waste fluid and debris, during use. Accordingly, embodiments of the device may include irrigation ports 37 coupled to a pump, such as a vacuum pump. The waste fluid may optionally be pumped to a reservoir or to a waste receptacle, such as a sink.

With reference to FIGS. 2 and 11, the ultrasonic driver 102 may be contained in a housing 55, 55*a* from which an eyelid contacting portion 30, 30*a*, 30*a*, 30*b*, 30*c* projects. The ultrasonic driver 102 is physically coupled, such as through a shaft, to the eyelid contacting portion such that ultrasonic energy from the ultrasonic driver 102 is transferred to the eyelid contacting portion. An exemplary ultrasonic driver is a piezoelectric driver. The piezoelectric driver may cause the eyelid contacting portion to oscillate as a frequency that ranges between about 10 kHz to about 100 kHz. In the embodiments illustrated in FIGS. 2 and 11, the ultrasonic driver 102 is provided in addition to the electrodes. However, it will be appreciated that the device may include ultrasonic driver without electrodes for delivering electrical energy to the eyelid.

During use, the eyelid contacting portion is brought into contact with the external portion of the upper eyelid, the external portion of the lower eyelid, the upper eyelid margin between the external surface of the upper eyelid and the internal surface of the upper eyelid, the lower eyelid margin between the external surface of the lower eyelid and the internal surface of the lower eyelid, the internal surface of the upper eyelid, the internal surface of the lower eyelid or combinations thereof. It is further appreciated that the eyelid contacting portion simultaneously contacts the relevant portion of the eyelid as described in the previous sentence across at least fifty percent of the width of the eyelid. In another embodiment, the eyelid contacting portion contacting portion contacts the relevant portion of the eyelid across at least seventy five percent of the width of the eyelid. In another embodiment, the eyelid contacting portion contacting portion contacts the relevant portion of the eyelid across at least ninety percent of the width of the eyelid. The width of the eyelid being defined as the portion of either the upper or lower eyelid that extends between the medial commissure and the lateral commissure. The ultrasonic driver 102 is activated and ultrasonic energy is applied to the at least one of the eyelid surfaces as well as to debris located thereon by the eyelid contacting portion.

In an embodiment, ultrasonic energy is applied without the application of any other form of energy to disrupt debris. In another embodiment, the ultrasonic energy is applied in combination with another form of energy to disrupt debris. For example, ultrasonic energy may be applied in combination with electrical energy to disrupt debris. In an embodiment, the ultrasonic energy may be applied at the same time as the other form of energy, such as electrical energy. In another embodiment, the ultrasonic energy and the other form of energy, such as electrical energy, are not applied at the same time. For example, ultrasonic energy and the other form of energy, such as electrical energy, may be applied in an alternating manner, or one of these forms of energy may be applied first and the other form of energy may be applied second. This alternating pattern may be repeated. In an embodiment, the other form of energy, such as electrical energy, is applied first and the ultrasonic energy is applied second. In another embodiment, the ultrasonic energy is applied first and the other form of energy, such as electrical energy, is applied second. The ultrasonic energy is applied for a duration and at a frequency sufficient to disrupt debris on the eyelid, and in particular debris on the eyelid margin.

Figure 14:
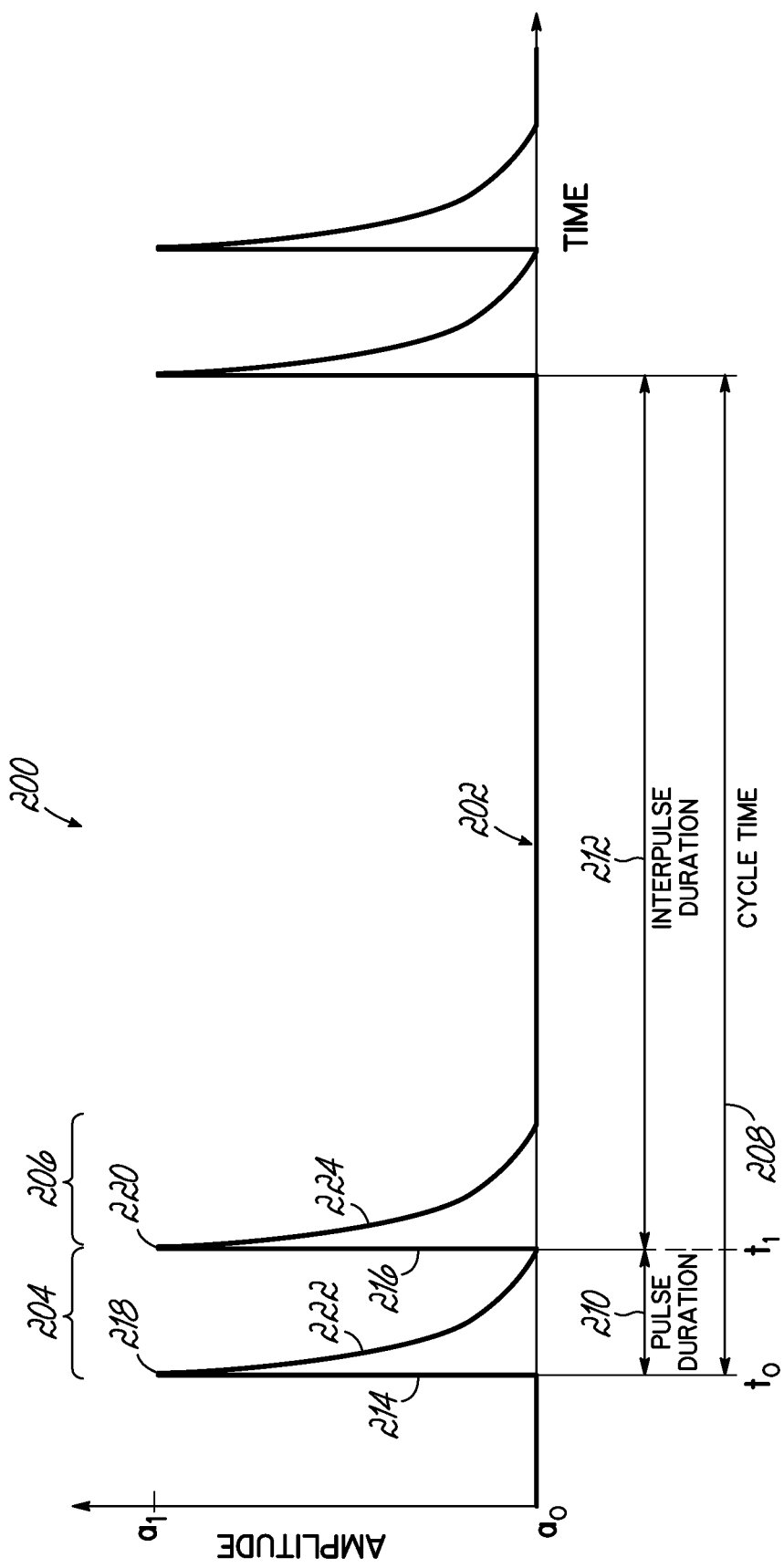
FIG. 14 is a graphical view of a twin peak monophasic waveform for use with the eye contacting portion of the instrument of FIG. 2.

FIG. 14 depicts a graph 200 that shows an exemplary monophasic waveform 202 which may be used to provide electrical energy to the eye contacting portion 30 of device 10. The monophasic waveform 202 may include a plurality of pulses (e.g., an initial pulse 204 and subsequent pulse 206) that repeat over a cycle time 208 and which can be used to electrolytically disrupt debris on an eyelid margin. Each pulse 204, 206 may have a pulse duration 210 and an interpulse duration 212 that collectively define the cycle time 208 of monophasic waveform 202. Each pulse 204, 206 may have a relatively short rise time 214, 216 during which the amplitude of the monophasic waveform 202 rises from an initial baseline amplitude $a_0$, (e.g., zero volts or amps) to a peak 218, 220 having a peak amplitude $a_1$, and fall time 222, 224 during which the amplitude of the monophasic waveform 202 falls back toward the baseline amplitude $a_0$, e.g., by decaying at a generally exponential rate.

Prior to time $t_0$, the monophasic waveform 202 may be at the initial baseline amplitude $a_0$. At the beginning of the cycle time 208, the amplitude of the monophasic waveform may begin rising and reach the initial peak 218 in a relatively short period of time, e.g., 1 µs. After reaching the initial peak 218, the amplitude of the monophasic waveform 202 may drop back toward the baseline amplitude $a_0$ over a period of time. The drop in the amplitude may be exponential in nature as the electrical energy dissipates into the patient. The period between peaks 218, 220 may be selected to allow the amplitude of the monophasic waveform to essentially return to the baseline amplitude $a_0$ before generating subsequent peak 220. At time $t_1$, the amplitude of the monophasic waveform 202 may begin to rise to subsequent peak 220, which may have the same amplitude $a_1$ as the initial peak 218. The amplitude of the monophasic waveform may then drop back toward the baseline amplitude $a_0$ over a period of time in similar manner as described for the initial peak 218. After the final pulse of the plurality of pulses, the monophasic waveform 202 may remain at baseline amplitude $a_0$ for the remainder of cycle time 208.

The amplitude of the monophasic waveform 202 may be characterized using current or voltage so that the baseline amplitude $a_0$ is zero volts or amps. For peaks 218, 220 characterized by voltage, the peak amplitude $a_1$ may be approximately 350V. For peaks 218, 220 characterized by current, the peak amplitude $a_1$ may be approximately 700 mA. An exemplary monophasic waveform 202 may have a cycle time 208 of approximately 10 ms and a pulse duration 210 of approximately 0.2 ms.

Figure 15:
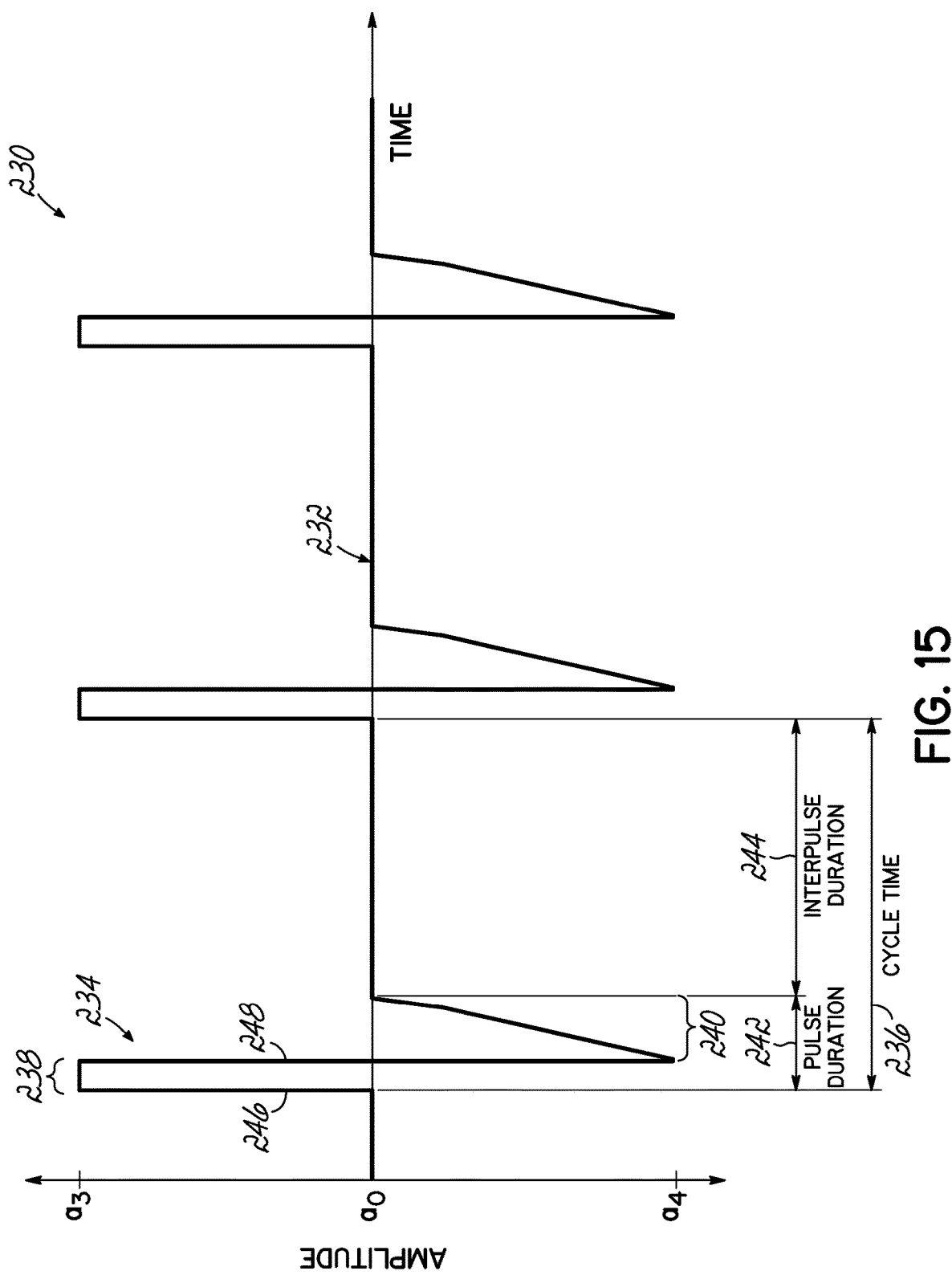
FIG. 15 is a graphical view of a biphasic asymmetrical waveform for use with the eye contacting portion of the instrument of FIG. 2.

FIG. 15 depicts a graph 230 that shows an exemplary biphasic waveform 232 that may be used to provide electrical energy to the eye contacting portion 30 of device 10. The biphasic waveform 232 may be assymetric, and may include a pulse 234 that repeats over a cycle time 236 and which can be used to electrolytically disrupt debris on an eyelid margin. Each pulse 234 may include a positive phase 238, a negative phase 240, and a pulse duration 242. The pulse duration 242 and an interpulse duration 244 may collectively define the cycle time 236 of biphasic waveform 232.

The positive phase 238 of pulse 234 may have a relatively short rise time 246 (e.g., 1 µS) during which the amplitude of the biphasic waveform 232 rises from the initial baseline amplitude $a_0$ to a positive peak amplitude $a_3$, and relatively short fall time 248 during which the amplitude of the biphasic waveform 232 falls toward a negative peak amplitude $a_4$. In an embodiment of the invention, the positive peak amplitude $a_3$ may have about the same magnitude as the negative peak amplitude $a_4$. The positive phase 238 may comprise a portion (e.g., about a third) of the pulse 234 during which the amplitude of biphasic waveform 232 is held at the positive peak amplitude $a_3$. During the negative phase 240 of pulse 234, the amplitude of the biphasic waveform 232 may decay or be driven toward the baseline amplitude $a_0$ at a generally linear rate from the negative peak amplitude $a_4$ back toward the baseline amplitude $a_0$ over the remaining portion of the pulse duration 242.

The amplitude of the biphasic waveform 232 may also be characterized using current or voltage. In cases where the biphasic waveform 232 is characterized by voltage, the peak amplitude $a_5$ may be in a range of approximately 0 to +50V, and the peak amplitude $a_4$ may be in a range of approximately 0 to −50V. In cases where the biphasic waveform 232 is characterized by current, the peak amplitude $a_5$ may be in a range of approximately 0 to +100 mA, and the peak amplitude $a_4$ may be in a range of approximately 0 to −100 mA. An exemplary biphasic waveform 232 may have a pulse duration 242 in a range of approximately 50 to 300 µs, and may be user adjustable in increments, e.g., 10 µs increments. The exemplary biphasic waveform may further include a cycle time 236 in a range of approximately 6.67 to 500 ms, yielding a frequency of 2-150 Hz, and may be adjustable in increments of frequency, e.g., 1 Hz increments.

Figure 16:
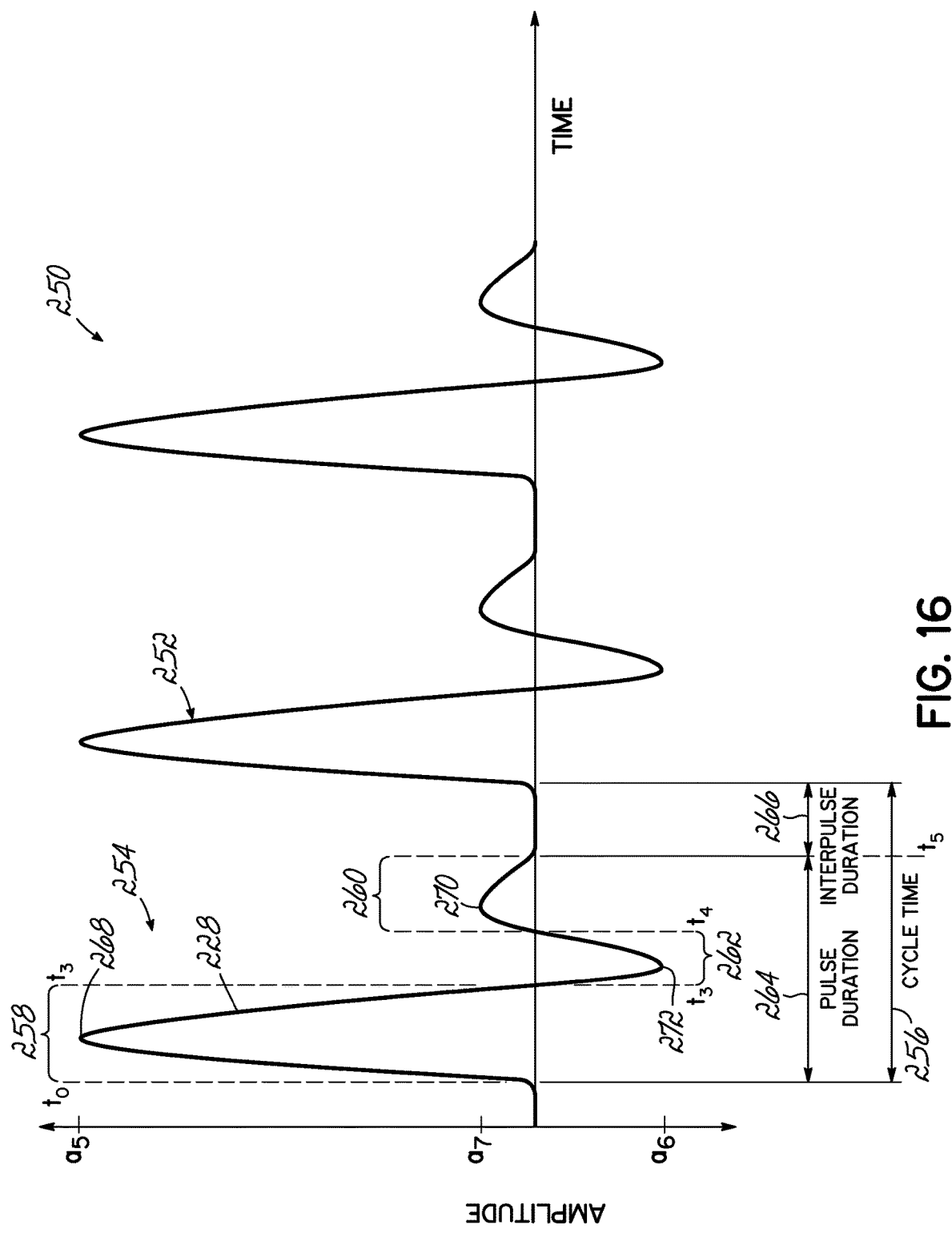
FIG. 16 is a graphical view of an unbalanced triphasic waveform for use with the eye contacting portion of the instrument of FIG. 2.

FIG. 16 depicts a graph 250 that shows an exemplary triphasic waveform 252 that may be used to provide electrical energy to the eye contacting portion 30 of device 10. The triphasic waveform 252 may include a pulse 254 that repeats over a cycle time 256 and which can be used to electrolytically disrupt debris on an eyelid margin. Each pulse 254 may include two positive phases 258, 260, a negative phase 262, and a pulse duration 264. The pulse duration 264 and an interpulse duration 266 may collectively define the cycle time 256 of triphasic waveform 252.

The initial positive phase 258 may have a peak 268 that predominates over peak 270 of subsequent positive phase 260 and over peak 272 of negative phase 262. That is, the amplitude $a_5$ of peak 268 may be greater than the amplitudes $a_6$, $a_7$ of the subsequent peaks 270, 272. Each of the phases 258, 260, 262 may have a generally sinusoidal shape with peak amplitudes $a_5$, $a_6$, $a_7$ that follow a generally exponential decay rate as compared to the preceding peaks 268, 270, 272.

Prior to time $t_0$, the triphasic waveform 252 may initially be at the baseline amplitude $a_0$. At the beginning of the cycle time 256, the amplitude of the triphasic waveform 252 may rise to positive peak 268 following a generally sinusoidal curve. The amplitude of the triphasic waveform 252 may then drop below the baseline amplitude $a_0$ over a period of time following a generally sinusoidal curve to reach negative peak 272 between zero-crossing times $t_3$ and $t_4$. The amplitude of the triphasic waveform 252 may then begin to rise above the baseline amplitude $a_0$ over a period of time following a generally sinusoidal curve to reach positive peak 270 between zero-crossing times time to and $t_5$. Each peak 270, 272 may have a reduced magnitude in comparison to the magnitude of the immediately preceding peak 268, 270. After reaching peak 270, the amplitude of the triphasic waveform 252 may drop toward the baseline amplitude $a_0$ over a period of time and remain there for the remainder of cycle time 256.

Figure 17:
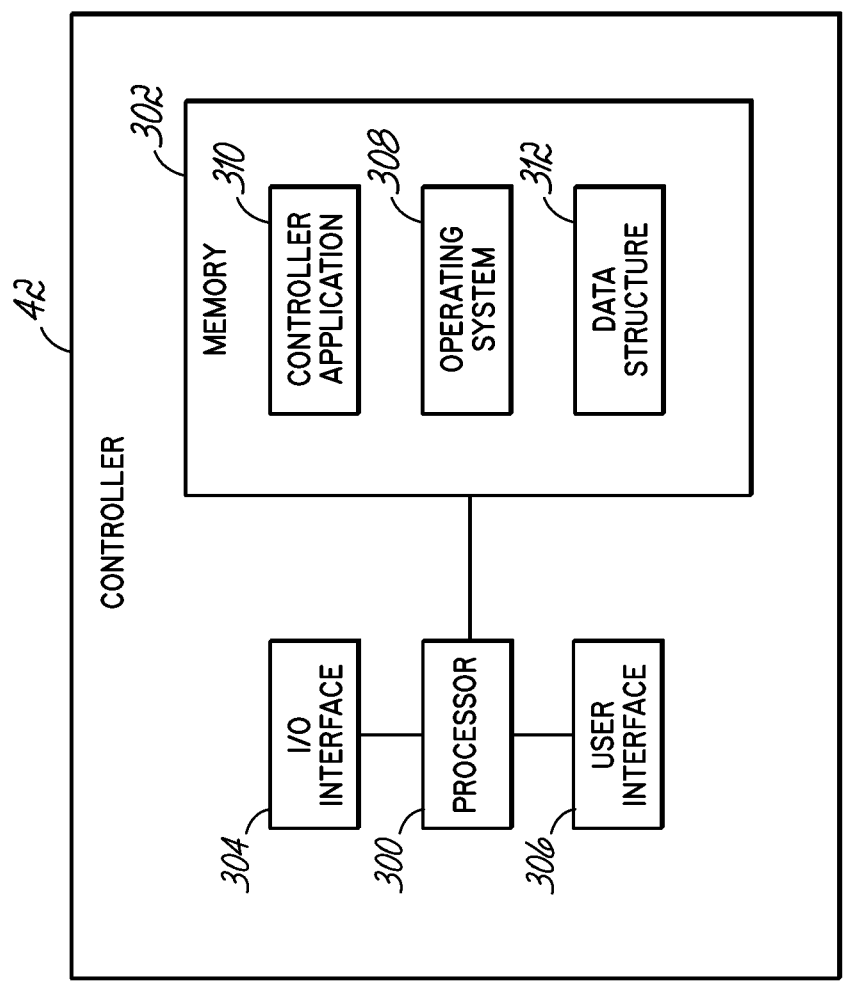
FIG. 17 is a diagrammatic view of an exemplary embodiment of the controller of FIGS. 3 and 8.

FIG. 17 depicts an exemplary controller 42 in accordance with an embodiment of the invention. The controller 42 may include a processor 300, a memory 302, an input/output (I/O) interface 304, and a user interface 306. The processor 300 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 302. Memory 302 may be a single memory device or a plurality of memory devices including but not limited to read-only memory (ROM), random access memory (RAM), volatile memory, non-volatile memory, static random access memory (SRAM), dynamic random access memory (DRAM), flash memory, cache memory, or any other device capable of storing digital information. Memory 302 may also include a mass storage device (not shown) such as a hard drive, optical drive, tape drive, non-volatile solid state device or any other device capable of storing digital information.

Processor 300 may operate under the control of an operating system 308 that resides in memory 302. The operating system 308 may manage controller resources so that computer program code embodied as one or more computer software applications, such as a controller application 310 residing in memory 302 may have instructions executed by the processor 300. In an alternative embodiment, the processor 300 may execute the controller application 310 directly, in which case the operating system 308 may be omitted. One or more data structures 312 may also reside in memory 302, and may be used by the processor 300, operating system 308, and/or controller application 310 to store data.

The I/O interface 304 may operatively couple the processor 300 to other components of embodiments of the invention, such as electrodes 20, 20a, 20b, 20c, 22, 22a, 22b, 22c, 24, 24a, 26, 26a, pump 100, and/or vacuum pump 101. The I/O interface 304 may include signal processing circuits that condition incoming and outgoing signals so that the signals are compatible with both the processor 300 and the components to which the processor 300 is coupled. To this end, the I/O interface 304 may include analog-to-digital (A/D) and/or digital-to-analog (D/A) converters, voltage level and/or frequency shifting circuits, optical isolation and/or driver circuits, and/or any other analog or digital circuitry suitable for coupling the processor 300 to the other components of embodiments of the invention.

The user interface 306 may be operatively coupled to the processor 300 of controller 42 in a known manner to allow a system operator to interact with the controller 42. The user interface 306 may include a display such as a video monitor, alphanumeric displays, a touch screen, a speaker, and any other suitable audio and visual indicators capable of providing information to the system operator. User interface 306 may also include input devices and controls such as an alphanumeric keyboard, a pointing device, keypads, pushbuttons, control knobs, microphones, etc., capable of accepting commands or input from the operator and transmitting the entered input to the processor 300. In this way, user interface 306 may enable manual initiation or selection of system functions, for example, during system set-up, calibration, and chemical loading.

While the present invention has been illustrated by the description of one or more embodiments thereof, and while the embodiments have been described in considerable detail, they are not intended to restrict or in any way limit the scope of the appended claims to such detail. For example, one of ordinary skill will appreciate that each of the electrodes could be replaced with a plurality of smaller electrodes space apart so as to apply electrical energy sufficient to disrupt debris on the eyelid margin. Further, exemplary embodiments of the invention have been illustrated or described as utilizing direct current. Alternative embodiments of the inventions described herein may utilize alternating current. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A device for removing debris from an eyelid margin comprising an eye contacting portion comprising:
    a first electrode configured to contact an outer surface of a first eyelid of an eye;
    a second electrode configured to contact an outer surface of a second eyelid of the eye;
    a power supply applying an electrical current between the first electrode and the second electrode; and
    a shelf extending from the eye contacting portion, wherein the shelf extends in the space between the first electrode and the second electrode, and wherein the shelf separates the first eyelid from the second eyelid;
    wherein the electrical current removes the debris from an eyelid margin.

2. The device of claim 1, further comprising:
    a third electrode configured to contact an eyelid margin of the first eyelid; and
    a fourth electrode configured to contact an eyelid margin of the second eyelid,
    wherein the third electrode and the fourth electrode are electrically coupled to the power supply.

3. The device of claim 2, further comprising:
    a first channel comprising a first inner sidewall, a first base wall, and a first outer sidewall; and
    a second channel comprising a second inner sidewall, a second base wall, and a second outer sidewall;
    wherein the first electrode is on the first inner sidewall, and wherein the second electrode is on the second inner sidewall.

4. The device of claim 3, wherein the first inner sidewall is moveable relative to the first outer sidewall, the second inner sidewall is moveable relative to the second outer sidewall, or both.

5. The device of claim 3, wherein the third electrode is coupled to the first base wall, and wherein the fourth electrode is coupled to the second base wall.

6. The device of claim 5, further comprising:
    at least one nozzle and a reservoir,
    wherein the at least one nozzle is fluidly coupled to a reservoir.

7. The device of claim 3, wherein a nozzle, an irrigation port, or both are positioned on the first inner sidewall, the second inner sidewall, or both.

8. The device of claim 2, wherein the third electrode is coupled to a face of the shelf nearest the first electrode, and wherein the fourth electrode is coupled to a face of the shelf nearest the second electrode.

9. The device of claim 2, wherein the first electrode and the fourth electrode have the same polarity and wherein the second electrode and the third electrode have the same polarity.

10. The device of claim 1, further comprising an ultrasonic driver coupled to an eyelid contacting portion.

11. The device of claim 10, wherein the ultrasonic driver comprises a piezoelectric driver.

12. The device of claim 10, wherein the ultrasonic driver oscillates at a frequency of about 10 kHz to about 100 kHz.

13. The device of claim 1, further comprising a nozzle and an irrigation port.

14. A system for removing debris from an eyelid margin comprising:
    the device of claim 13;
    a reservoir; and
    a pump, wherein the pump transmits a washing solution, an electrolyte solution, or both from the reservoir to the nozzle, transmits a waste fluid from the irrigation port to the resevoir, or both.

15. The device of claim 1, wherein voltage of the electrical current is about 0.1 V to about 20 V.

16. The device of claim 1, wherein the electrical current is less than about 3 milliamps.

17. The device of claim 1, wherein the electrical current is a direct current.

18. The device of claim 1, wherein the electrical current is an alternating current.

19. The device of claim 1, wherein polarity of the first electrode and polarity of the second electrode are reversible.

20. A device for removing debris from an eyelid margin comprising an eye contacting portion comprising:
    a first electrode configured to contact an outer surface of a first eyelid of an eye;
    a second electrode configured to contact an outer surface of a second eyelid of the eye;
    a power supply applying an electrical current between the first electrode and the second electrode;
    a first channel comprising a first inner sidewall, a first base wall, and a first outer sidewall; and
    a second channel comprising a second inner sidewall, a second base wall, and a second outer sidewall, wherein the first channel and the second channel separate the first eyelid from the second eyelid;
    wherein the electrical current removes the debris from the eyelid margin; and
wherein the first inner sidewall is moveable relative to the first outer sidewall, wherein the second inner sidewall is moveable relative to the second outer sidewall, or both.

* * * * *